(12) United States Patent
Chikusa et al.

(10) Patent No.: US 8,158,072 B2
(45) Date of Patent: Apr. 17, 2012

(54) ANALYSIS APPARATUS AND ANALYSIS METHOD OF CHLOROSILANES

(75) Inventors: Noboru Chikusa, Yokkaichi (JP); Masaki Itoh, Yokkaichi (JP)

(73) Assignee: Mitsubishi Materials Corporation, Tokyo (JP)

( * ) Notice: Subject to any disclaimer, the term of this patent is extended or adjusted under 35 U.S.C. 154(b) by 72 days.

(21) Appl. No.: 12/462,945

(22) Filed: Aug. 11, 2009

(65) Prior Publication Data

US 2010/0041157 A1 Feb. 18, 2010

(30) Foreign Application Priority Data

Aug. 12, 2008 (JP) ................................. 2008-208211
Aug. 3, 2009 (JP) ................................. 2009-181057

(51) Int. Cl.
*G01N 33/00* (2006.01)
*B01J 19/00* (2006.01)
(52) U.S. Cl. ......................................... 422/198; 436/72
(58) Field of Classification Search .................... 436/72; 422/102, 198
See application file for complete search history.

(56) References Cited

U.S. PATENT DOCUMENTS

| 5,224,775 A * | 7/1993 | Reading et al. .................. 374/11 |
| 2007/0065933 A1* | 3/2007 | Esser et al. .................. 435/286.6 |
| 2007/0157876 A1* | 7/2007 | Minemoto et al. ............ 117/109 |

FOREIGN PATENT DOCUMENTS

| JP | 02-013834 | 1/1990 |
| JP | 03-172759 | 7/1991 |
| JP | 2002-005799 | 1/2002 |

* cited by examiner

*Primary Examiner* — Jill Warden
*Assistant Examiner* — Dwan A Gerido
(74) *Attorney, Agent, or Firm* — Edwards Wildman Palmer LLP

(57) ABSTRACT

The problem to be solved is to provide an analysis apparatus and analysis method of chlorosilanes capable of stably carrying out an analysis with less contamination. An analysis apparatus of chlorosilanes includes a vaporizer 10 for vaporizing chlorosilanes L and an analyzer for analyzing materials r1 and r2 remained by vaporizing. In the analysis apparatus, the vaporizer 10 includes a hotplate 11, a cover 12 detachably attached onto the hotplate 11 and configuring a heating chamber 13 with the hotplate 11, and a sample vessel 14 arranged in the heating chamber 13 and having an opening upside capable of storing the chlorosilanes L. The cover 12 includes a supply port 12a for supplying an inert gas or nitrogen gas into the heating chamber 13 and a discharge port 12b for discharging gases in the heating chamber 13.

14 Claims, 8 Drawing Sheets

ANALYSIS APPARATUS AND ANALYSIS METHOD OF CHLOROSILANES

BACKGROUND

1. Field of the Invention

The present invention relates to an analysis apparatus and analysis method of chlorosilanes.

This application claims priority on Japanese Patent Application No. 2008-208211, filed on Aug. 12, 2008, the content of which is incorporated herein by reference.

2. Conventional Art

Chlorosilanes, such as trichlorosilane, tetrachlorosilane, and the like, are used for a raw material of polycrystalline silicon, a semiconductor, e.g., an epitaxial film of a silicon wafer, and a raw material of an optical fiber. In these applications, chlorosilanes with extremely low level of metal contaminations, namely, Fe, Ni, Cr, Al, Cu, Zn, and the like, are required. Further, samples of the chlorosilanes, which are almost free from an influence of these metal contaminations, are essential for evaluating qualities of the chlorosilanes.

As a conventional technique for analyzing chlorosilanes, the patent document 1 discusses a technique in which a chlorosilane solution is diluted with argon gas, and a high-frequency inductively-coupled plasma emission analysis method is used. Also the patent document 2 discusses a technique in which moisture in a silane gas is removed, and the silane gas is introduced to a discharge type photoionization detector through a predetermined device.

However, the chlorosilanes, which passed through no condensing process, are directly measured in the techniques discussed in these patent documents. Therefore, main components in a sample may often disturb a detection of the metal contaminations, and then high analysis sensitivity is not available in these techniques. For example, the patent document 3 discusses a technique for analyzing a photoresist developer in order to carry out an analysis with higher sensitivity. In this technique, vaporizing a sample in a sample vessel, the main components are eliminated, and also contaminations are condensed. The condensed contaminations are analyzed by an inductively-coupled plasma mass spectrometry. However, in this method, the use of a microwave as a heating source makes the apparatus structure complicated.

Further, in case that a plurality of sample vessels to be measured are arranged in the chamber at once, the pipe arrangements for supplying an inert gas to each sample vessel become complicated, too. Thus, this method is inconvenient for measuring many samples concurrently.

[Prior Art Documents]
[Patent Documents]
[Patent Document 1] Japanese Patent Application Laid-Open No. 2-13834
[Patent Document 2] Japanese Patent Application Laid-Open No. 3-172759
[Patent Document 3] Japanese Patent Application Laid-Open No. 2002-5799

SUMMARY OF THE INVENTION

Problems to be Solved by the Invention

In the aforementioned analysis apparatuses, hydrogen chloride gases are generated, in case the chlorosilanes contact with the atmosphere, and then the gases corrode the apparatus. This corrosion causes problems, such as a deterioration of the analysis and a malfunction of the apparatuses.

Further, when silica ($SiO_2$) is generated in the condensing process by the vaporized chlorosilanes, the silica causes a malfunction in which the pipe arrangement of the analysis apparatus is clogged with the silica.

Furthermore, when the silica adhering to a vaporization vessel is re-melted, its silicon component disturbs a detection of the metal contaminations. Thus a problem, in which an analysis sensitivity of the apparatus becomes poor, rises.

The present invention is to solve the aforementioned problems and aims to provide an analysis apparatus and analysis method of chlorosilanes having an ability to carry out a stable analysis with less contamination by using a simple heating means and an inert gas supply means.

Means for Solving the Problems

According to an aspect of the present invention to achieve the aforementioned aims, an analysis apparatus of chlorosilanes includes
an vaporizer for vaporizing chlorosilanes and
an analyzer for analyzing evaporation residues, namely, remainders after vaporizing.
In the apparatus, the vaporizer includes a hotplate,
a cover detachably attached onto the hotplate composing a heating chamber together with the hotplate, and
one or more of sample vessel(s),
in which their upside are open to store the chlorosilanes in them, arranged in the heating chamber.
The cover includes
a supply port for supplying an inert gas into the heating chamber and
a discharge port for discharging the gas in the heating chamber.
Further, an analysis method of chlorosilanes according to the present invention includes
a vaporization process for vaporizing chlorosilanes and
an analysis process for analyzing an evaporation residue.
In the vaporization process,
the chlorosilanes are stored in the sample vessels,
the sample vessels are arranged in the heating chamber, and then
the heating chamber is heated up with an inert gas flowing through the heating chamber.

According to the present invention, supplying and discharging an inert gas concurrently, the chlorosilanes are vaporized in the heating chamber.

Therefore, this method can prevent a generation of a corrosive gas and $SiO_2$ around the samples in the vaporization process; and also can prevent a deterioration of the analysis sensitivity, a malfunction of the apparatus, and contamination of the samples.

In the analysis apparatus of chlorosilanes, a heating face of the hotplate, an inner face of the cover, and the sample vessel are preferably made of a fluoride type resin.

In this case, since the heating face of the hotplate, the inner face of the cover, and the sample vessel are made of a fluoride type resin which is free from corrosion by the chlorosilanes, the inside of the heating chamber can be prevented from corrosion. Therefore, contamination of the sample due to corrosion in the heating chamber or the like can be prevented.

In the analysis apparatus of chlorosilanes, the supply port and the discharge port are preferably located at higher places than positions of upper ends, namely, upper brims, of the sample vessels.

In this case, when chlorosilanes is vaporized, the vaporized chlorosilanes in the sample vessels can be discharged efficiently from the heating chamber. Thus, the apparatus and the samples can be effectively prevented from contamination.

In the analysis method of chlorosilanes, the vaporization process is preferable conducted in the state wherein a plurality of the sample vessels stored with the chlorosilanes are arranged in the heating chamber together with a plurality of the vessels without the chlorosilanes, i.e. empty, as the reference vessels during this process.

In this case, the evaporation residues, which are on the reference vessels after the vaporization process, are considered as products depending on an environment in the heating chamber. Further, the samples, which are processed together with the reference vessels in situ, should be affected by the same environment, too.

Therefore, the chlorosilanes can be analyzed more accurately by considering an influence of the environment from the residues on the reference vessels.

After the vaporization process, each quantity of the contaminations in the residues on the reference vessels is analyzed. If an average and/or a standard deviation calculated from the quantity are not within predetermined control values; since the residues on the sample vessels also must be significantly affected by the environment, the results of analyzing the residues on the sample vessels should be discarded. Thus, the results of analyzing with a less influence from a measuring environment can be obtained.

Effectiveness of the Invention

The analysis apparatus and method of chlorosilanes in the present invention can prevent a sample from contamination in the process for vaporizing chlorosilanes. Thus an analysis, which is free from influences of contaminations in the sample preparation step, can be accurately and stably carried out.

DETAILED DESCRIPTION OF THE EMBODIMENT

Exemplary embodiments of an analysis apparatus of chlorosilanes according to the present invention will be described below referring to Figs.

Figure 1:
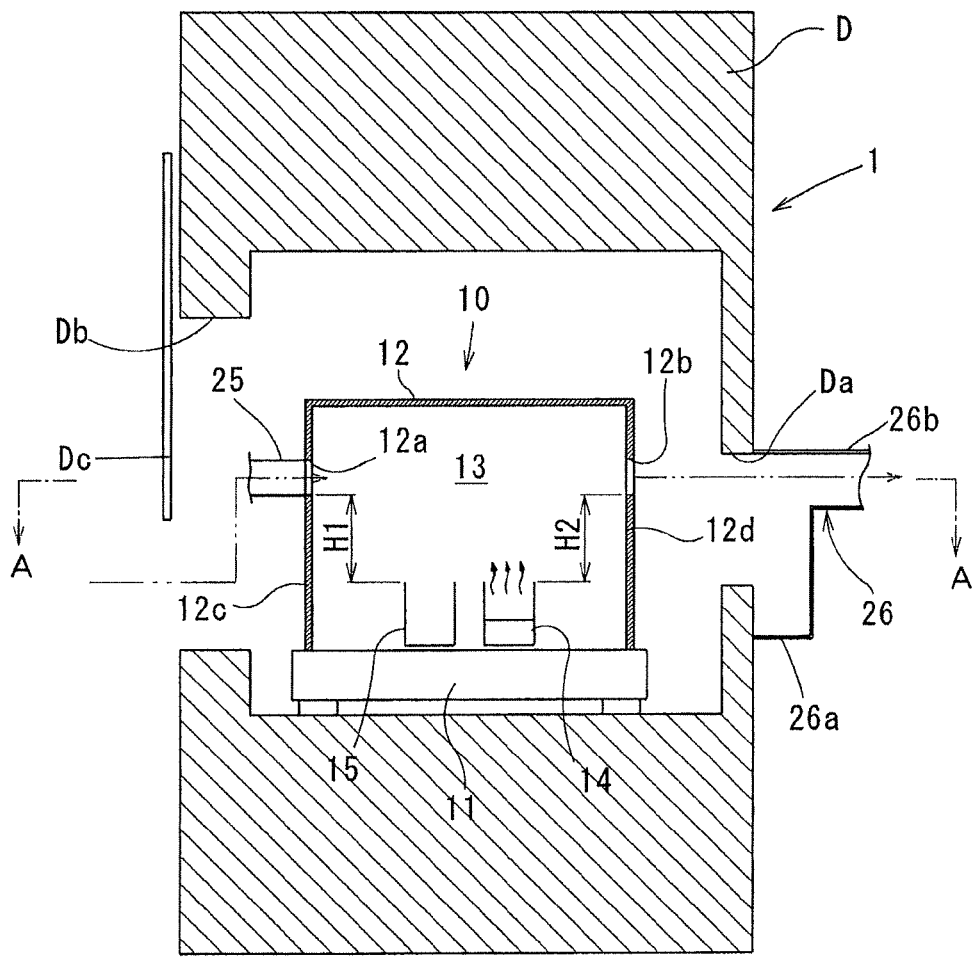
FIG. 1 is a schematic longitudinal cross-sectional view illustrating the first exemplary embodiment of an analysis apparatus of chlorosilanes of the present invention.
Figure 2:
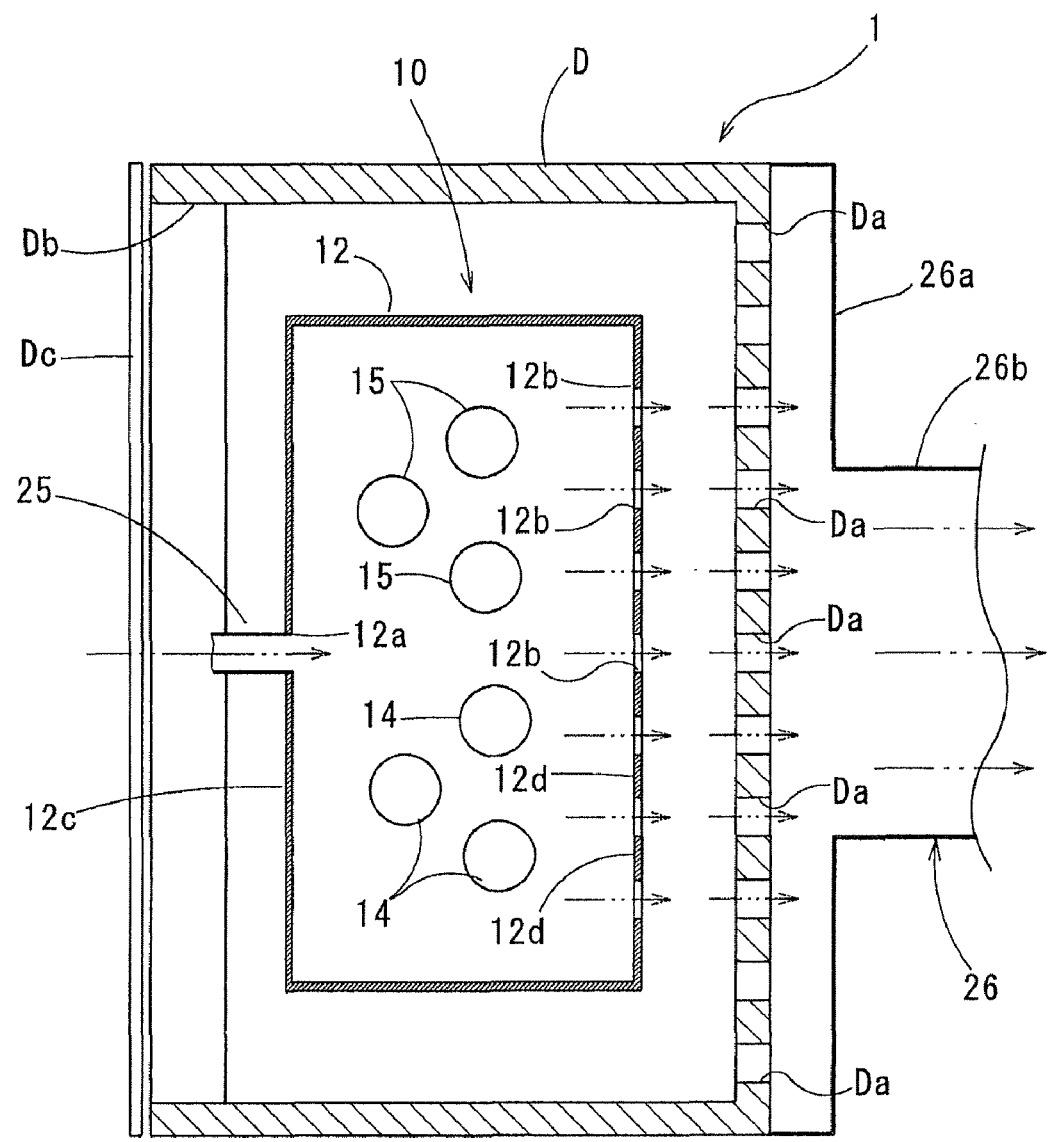
FIG. 2 is a transverse cross-sectional view taking along a line A-A of the analysis apparatus illustrated in FIG. 1.

FIGS. 1 and 2 illustrate an analysis apparatus 1 of chlorosilanes of a first exemplary embodiment of the present invention. In this analysis apparatus 1, a vaporizer 10 is provided in a draft chamber D. The vaporizer 10 includes a hotplate 11 and a cover 12 detachably attached to an upper part of the hotplate 11. A heating chamber 13 is comprised of the hotplate 11 and the cover 12. Further, the vaporizer 10 includes a plurality of sample vessels 14 and reference vessels 15 (three in this exemplary embodiment each other) which are arranged on the hotplate 11 in the heating chamber 13. In this case, a heating face (an upper face) of the hotplate 11 is coated with a fluoride type resin. Further, the cover 12, the sample vessels 14, and the reference vessels 15 are made of a fluoride type resin. In addition, the sample vessel 14 and the reference vessel 15 are beakers with the same shape, made of the same materials, and their upsides are open.

The hotplate 11 is a heater wherein the temperature of its whole upper face can be increased to a high range, and then the hotplate 11 can heat up the sample vessels 14 and the reference vessels 15 directly.

The cover 12 has a box-like shape, and its lower face is open. One supply port 12a for supplying an inert gas, for example nitrogen gas, into the heating chamber 13, and a plurality of discharge ports 12b for discharging gasses in the heating chamber 13 to an external of the heating chamber 13 are provided on the side faces of the cover 12.

The supply port 12a is located at a higher place vertically than positions of upper ends, namely, upper brims, of the sample vessels 14 and the reference vessels 15 which are arranged into the heating chamber 13; and is at a distance H1 (>0) from these upper ends.

Similarly, the discharge ports 12b are also located at a higher place vertically than positions of upper ends, namely, upper brims, of the sample vessels 14 and the reference vessels 15; and are at a distance H2 (>0) from these upper ends.

The supply port 12a and the discharge ports 12b are arranged on side walls 12c and 12d which are facing each other, and each discharge port 12b is arranged in a line in a horizontal direction at a same height on the side wall 12d. For example, a height of the cover 12 is 100 mm and heights of the sample vessels 14 and the reference vessels 15 are 60 mm respectively. A height up to a lower edge of the supply port 12a and a height up to lower edges of the discharge ports 12b are 70 mm respectively. Therefore, H1 is equal to 10 mm (H1=10 mm) and H2 is equal to 10 mm (H2=10 mm).

Further, the discharge ports 12b are arranged for facing a plurality of duct holes Da formed at a rear part of the draft chamber D.

In this exemplary embodiment, nitrogen gas is introduced and supplied by a pipe arrangement 25 from an external of the draft chamber D to the heating chamber 13 through the supply port 12a.

Charging nitrogen gas into the heating chamber 13, the gas supplied in the heating chamber 13 makes a gas flow and goes toward the discharge ports 12b as a flow going to a fixed direction together with a vapor of vaporized chlorosilanes derived from the sample vessel 14.

A gas discharged from the heating chamber 13 flows into duct holes Da of the draft chamber D through the discharge ports 12b and is sent to an exhaust gas treatment facility (a scrubber, not illustrated in the drawings) provided at an external through a duct pipe arrangement 26 connected with the duct holes Da.

As illustrated in FIG. 2, this duct pipe arrangement 26 includes a header cover part 26a surrounding every outer side openings of the duct holes Da of the draft chamber D as one unit, and a pipe arrangement part 26b which goes from a center part in a width direction of the header cover 26a to the exhaust gas treatment facility.

In addition, a door Dc capable of opening and closing a front opening part Db is provided at a front part of the draft chamber D.

According to the analysis apparatus 1 of the present invention having the aforementioned configuration, since the heating face of the hotplate 11 and the cover 12 are made of a fluoride type resin, the apparatus is free from corrosion by a vapor of chlorosilanes, and then a sample is also free from contamination by a corroded material.

Further, since the inside of the heating chamber 13 is filled with nitrogen gas, the nitrogen gas prevents the reaction shown in the following formulas, which occurs in case chlorosilanes contact with the atmosphere, and then produces a corrosive gas and $SiO_2$ from the chlorosilanes and atmospheric moisture.

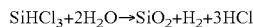

$$SiHCl_3 + 2H_2O \rightarrow SiO_2 + H_2 + 3HCl$$

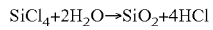

$$SiCl_4 + 2H_2O \rightarrow SiO_2 + 4HCl$$

Therefore, the sample can be prevented from contamination, and thus a stable analysis with high purity can be carried out.

Then, an analysis method of chlorosilanes as the present invention using the analysis apparatus 1 having the aforementioned configuration will be described below, referring to FIGS. 3 through 7. The analysis method includes a vaporization process for vaporizing chlorosilanes and an analysis process for analyzing the evaporation residues.

Figure 3:
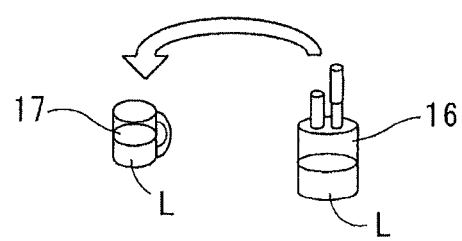
FIG. 3 is a schematic view showing a preparative isolation method of a sample solution in an analysis method using the analysis apparatus illustrated in FIG. 1.

In the vaporization process, as illustrated in FIG. 3, a chlorosilane sample solution L is taken from a quartz bottle 16 to a sampling cup 17, and the chlorosilane sample solution L is measured and divided onto three sample vessels 14 to be equal amounts (40 ml in this exemplary embodiment) from the sampling cup 17. On the other hand, the reference vessels 15 remain empty.

Figure 4:
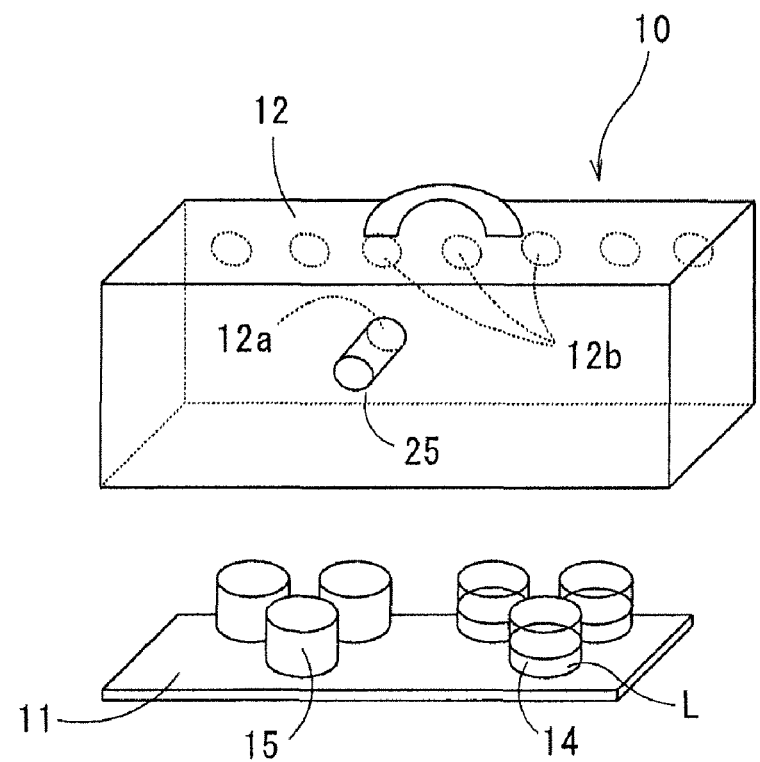
FIG. 4 is a schematic perspective view illustrating a state that a sample vessel and a reference vessel are provided on a hotplate in an analysis method using the analysis apparatus illustrated in FIG. 1.
Figure 5:
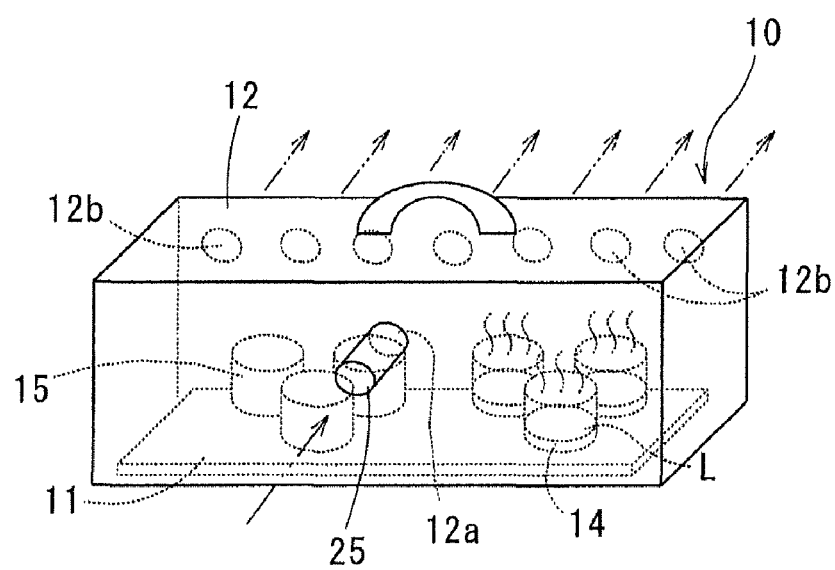
FIG. 5 is a schematic perspective view illustrating a state at a vaporization process in an analysis method using the analysis apparatus illustrated in FIG. 1.

Then, as illustrated in FIG. 4, each sample vessel 14 and each reference vessel 15 are arranged on the upper face of the hotplate 11 located in the draft chamber D. Further the cover 12 is put to cover the sample vessels 14 and the reference vessels 15. That is, the sample vessels 14 and the reference vessels 15 are arranged in the heating chamber 13 comprised of the hotplate 11 and the cover 12 (FIG. 5).

The chlorosilane sample solution L stored in the sample vessels 14 is vaporized by heating the hotplate 11 while supplying nitrogen gas into the heating chamber 13 through the supply port 12a. The vapor of the chlorosilane sample solution L is discharged from the discharge ports 12b together with the nitrogen gas.

Figure 6:
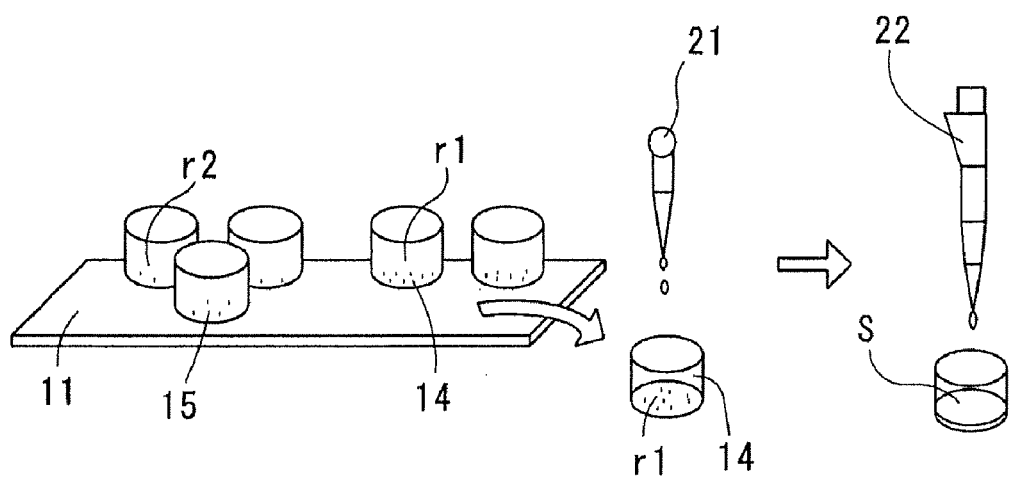
FIG. 6 is a schematic view illustrating a sample preparation procedure in an analysis method using the analysis apparatus illustrated in FIG. 1.

After this vaporization process, contamination in the chlorosilane sample solution L remains as a residue r1 on each sample vessel 14. Further a residue r2, which is derived from an influence of the environment, is found on the reference vessel 15 without the chlorosilane sample solution L (FIG. 6).

This residue r2 is a solidification which is from vaporized materials generated in the heating chamber 13 while the vaporization process and/or from materials in the gas. Therefore, the same solidification should exist in the residue r1 on each sample vessel 14 likewise.

Figure 7:
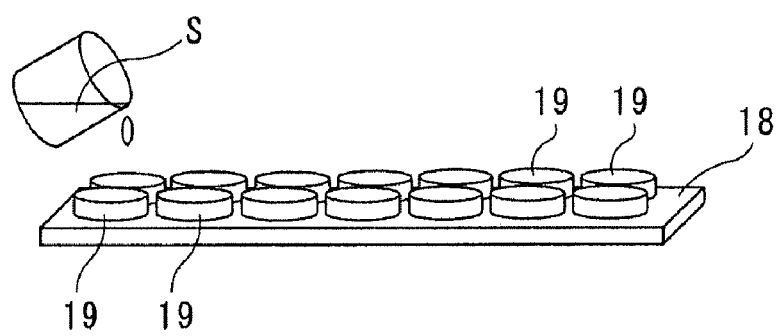
FIG. 7 is a schematic view illustrating a procedure for introducing a sample into an analyzer in an analysis method using the analysis apparatus illustrated in FIG. 1.

In the analysis process, these residues r1 and r2 are analyzed. As illustrated in FIG. 6, an sample for analyzing S is prepared by taking few drops of a solution containing nitric acid ($HNO_3$) and hydrogen fluoride (HF) at a ratio of 1:1 into each sample vessel 14 and each reference vessel 15 using a pipette 21, stirring the solution so as to solve the residues r1 and r2, adding pure water (a solution for dilution) of 10 ml to the solution using a micropipette 22 for diluting the solution. As illustrated in FIG. 7, each sample for analyzing S produced from each sample vessel 14 and each reference vessel 15 are taken into a plurality of sampling bottles 19 housed in a sampling bottle holder 18, and compositions are analyzed using an inductively-coupled plasma mass spectrometry analyzer.

A determination relating the result of analyzing each sample for analyzing S will be described.

At first, to examine the result, averages and standard deviations for each quantity of each contamination in the residues r2 on each reference vessel 15 are calculated from the result.

When processing the vaporization, the reference vessels 15 have not the chlorosilane sample solution L, i.e. the reference vessels 15 are empty. Thus the residue r2 is considered as products depending on an environment in the vaporization process.

Therefore, if the aforementioned standard deviations for the residues r2 are within predetermined control values; this result gives a conclusion that the vaporization process was conducted in good condition without significant problems caused by the environment during the vaporization process.

Next, each composition in the residue r1 on each sample vessel 14 is measured. The residue r1 should include the primary contaminations in the chlorosilane sample solutions on each vessels as well as the residues r2.

Therefore, quantity of a primary contamination in the samples is considered as a difference between an average for the residues r1 and an average for the residues r2.

If the aforementioned standard deviations for the residues r2 are not within predetermined control values, the vaporization environment and/or the measuring environment seem to be with any trouble(s).

In this case, since the analysis result also seems to be not reliable, this result must be discarded.

Further, any treatments for removing the factors; which are causing this large standard deviations, namely, contaminations on an inner face of the cover 12, on the face of the hotplate 11, on the sample vessels 14, and/or on the reference vessels 15, and/or causes of these contaminations; are required.

According to the analysis method of the present invention, the vaporization process is applied to the sample vessels 14 with the chlorosilane sample solution L and the reference vessels 15 which are empty. After the vaporization process, by conducting the analysis process in which the evaporation residues are analyzed relatively, factors of contamination caused by environment can be removed from the results; and then an analyzing result with high reliability can be acquired.

Figure 8:
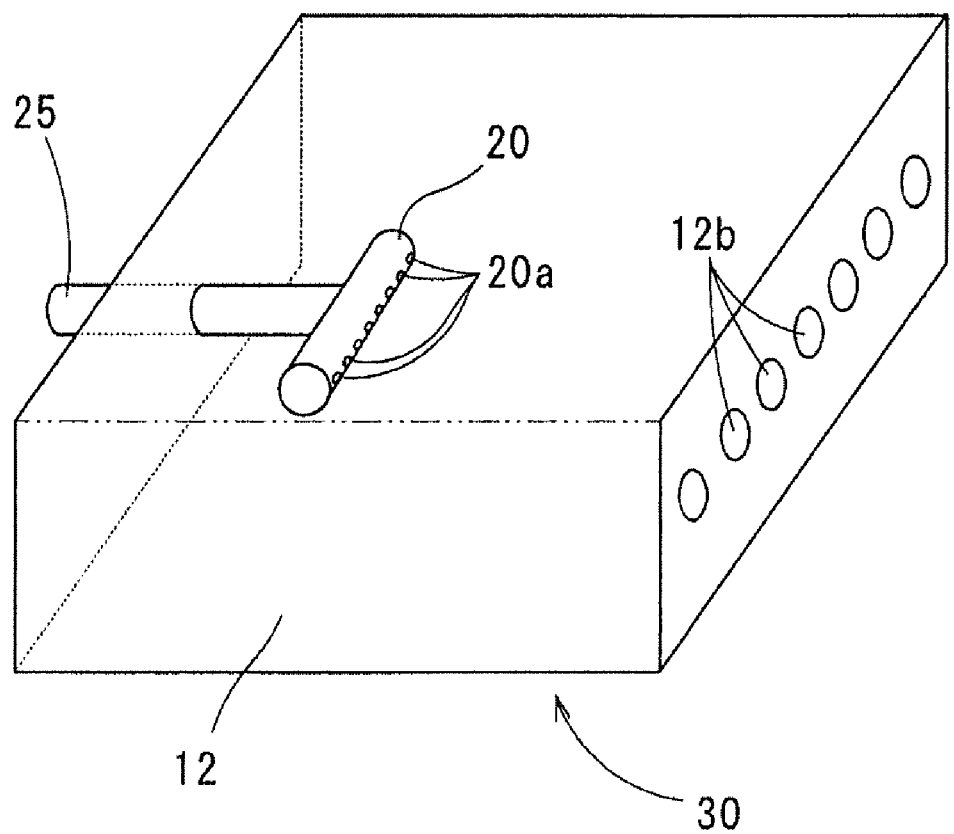
FIG. 8 is a schematic view illustrating a variation example of a vaporizer used in an analysis apparatus, seeing through the inside of the vaporizer.

In addition, the present invention is not limited in the configuration of the aforementioned exemplary embodiment and can be changed variously in a detailed configuration which does not depart from the objective of the present invention. For example, the supply port 12a for nitrogen gas is formed in a simple circular hole in the aforementioned exemplary embodiment. However, a nozzle 20 of an vaporizer 30 illustrated in FIG. 8 can be used, in which the nozzle 20 has a plurality of supply ports 20a provided in a line in a horizontal direction. In this case, since nitrogen gas can be supplied more uniformity into the heating chamber 13, a retention area of a nitrogen gas flow in the heating chamber 13 can be reduced so as to prevent generating a corrosion gas and SiO2 by a chlorosilane vapor more effectively, and can prevent contamination of the sample more accurately.

Figure 9:
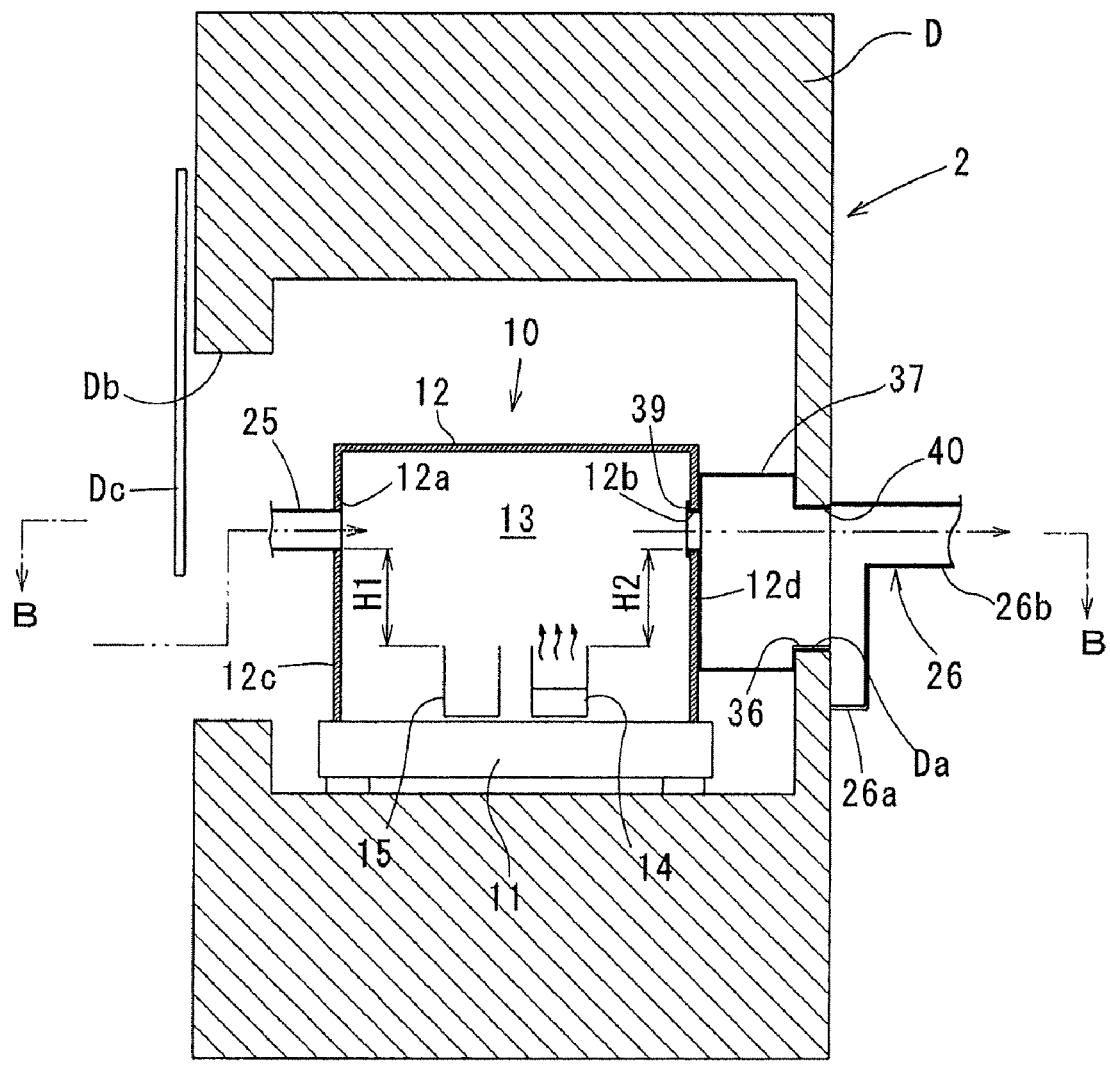
FIG. 9 is a schematic longitudinal cross-sectional view illustrating a second exemplary embodiment of an analysis apparatus of the present invention.
Figure 10:
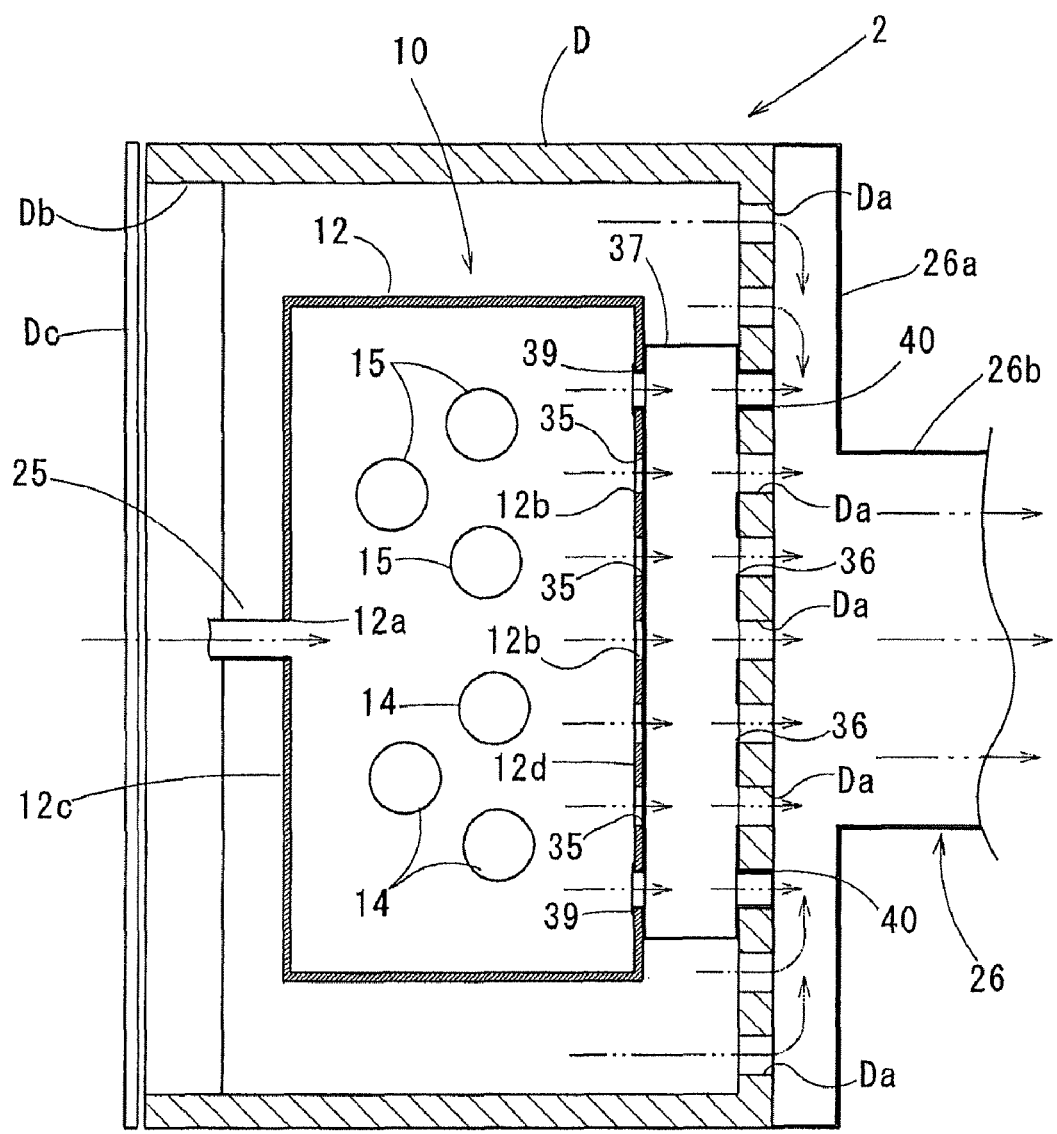
FIG. 10 is a transverse cross-sectional view taking along a line B-B of the analysis apparatus illustrated in FIG. 9.

Further, in the aforementioned exemplary embodiment, the discharge ports 12b of the cover 12 and the duct holes Da of the draft chamber D are only arranged for facing each other, but can be arranged to have a structure of a second exemplary embodiment illustrated in FIGS. 9 and 10. In an analysis apparatus 2 of the second exemplary embodiment, a box 37 having a plurality of holes 35 and 36 for communicating the discharge ports 12b and the duct holes Da is attached so as to connect from the discharge ports 12b of the cover 12 to the duct holes Da of the draft chamber D.

Chlorosilanes vaporized in the heating chamber 13 are discharged from the discharge ports 12b together with a gas flow of nitrogen gas supplied from the supply port 12a, and the atmosphere in the space, which is inside of the draft chamber D and is outside of the heating chamber 13, is sucked as illustrated with the arrows in FIG. 10 so as to flow from the duct holes Da to the duct pipe arrangement 26.

If the atmosphere in the draft chamber D contains much atmospheric moisture, this moisture may often reacts with the chlorosilanes contained in the nitrogen gas to form $SiO_2$.

The nitrogen gas, which is including the chlorosilanes and is discharged from the discharge ports 12b, goes through the inside of the box 37; and thus the box 37 prevents this gas from diffusing into the interior of the draft chamber D.

Further, the nitrogen gas blowing into the heating chamber 13 makes the interior of the heating chamber 13 positive pressure for the atmosphere. Also, the scrubber absorption makes the interior of the draft chamber D negative pressure for the atmosphere. Therefore, the silica generated in the draft chamber D can not flow backward into the heating chamber 13.

In this embodiment, the box 37 has cylindrical parts 39 arranged on both end parts in the width direction, and the cylindrical parts 39 and 40 are fitted into the discharge ports 12b in the cover 12. By fitting the cylindrical parts 39 and 40 into the inner sides of the discharge ports 12b and the inner sides of a duct hole Da, the box 37 is fixed on the cover 12 and the wall of the draft chamber D.

Figure 11:
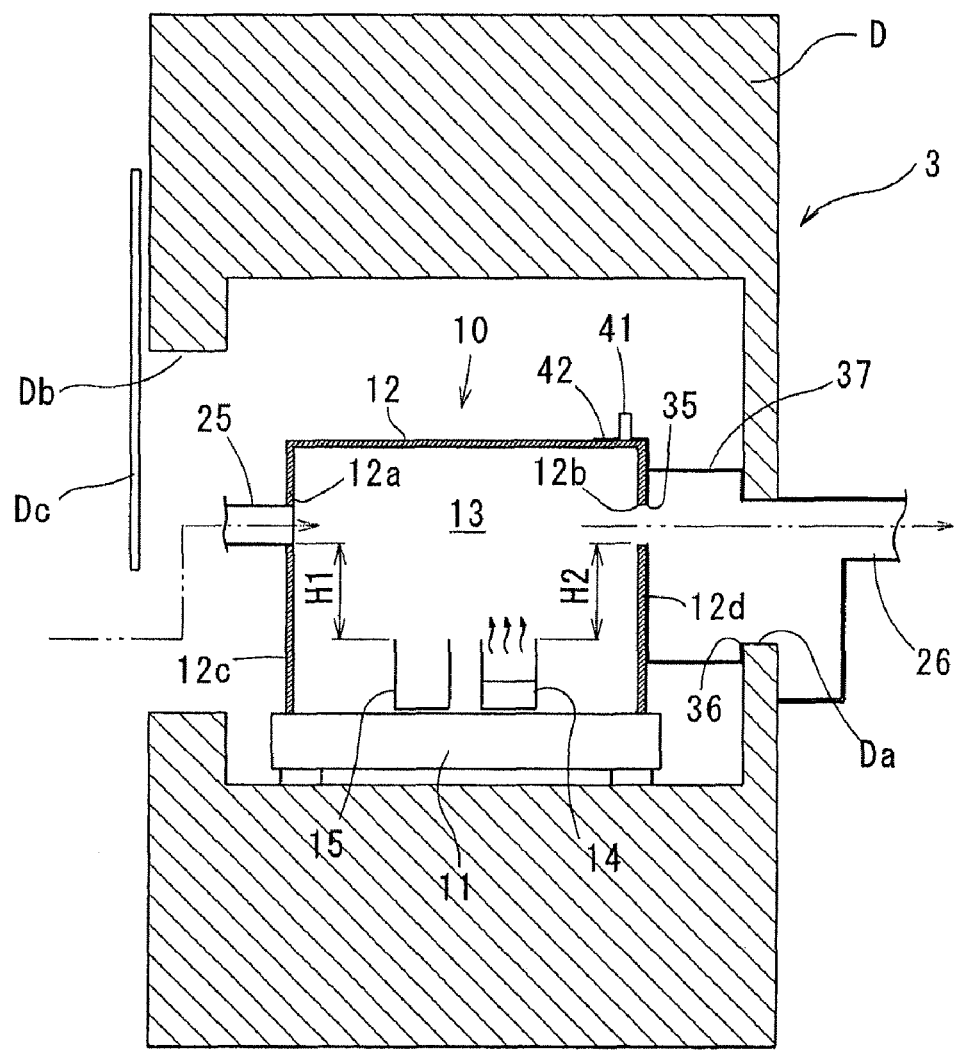
FIG. 11 is a schematic longitudinal cross-sectional view illustrating a third exemplary embodiment of an analysis apparatus of the present invention which is similar to FIG. 1.

Furthermore, FIGS. 9 and 10 illustrate an example in which a part of the box 37 (the cylindrical parts 39 and 40) is fitted into the discharge ports 12b of the cover 12 and the duct hole Da of the draft chamber D, and also is fixed on them. However, in an analysis apparatus 3 of a third exemplary embodiment illustrated in FIG. 11, a projection pin 41 is vertically provided on an upper wall of the cover 12, and the box 37 has a hook 42 to be engaged with the projection pin 41. In this embodiment, the box 37 is detachably hooked on the cover 12.

In addition, the design of the present invention can be properly changed within the objective of the present invention. Additionally, the vaporization process with only one sample vessel 14 is also usable. However, by arranging a plurality of the sample vessels 14 described in the aforementioned exemplary embodiment, the analysis can become more accurate.

EXPLANATION OF REFERENCE NUMERALS 1, 2, 3: Analysis apparatuses
10, 30: Vaporizer
11: Hotplate
12: Cover
12a: Supply port
12b: Discharge port
12c, 12d: Side wall
13: Heating chamber
14: Sample vessel
15: Reference vessel
16: Quartz bottle
17: Sampling cup
18: Sample bottle holder
19: Sample bottle
20: Nozzle
20a: Supply port
21: Pipette
22: Micropipette
25: Pipe arrangement
26: Duct pipe arrangement
26a: Header cover part
26b: Pipe arrangement part
35, 36: Holes
37: Box
39: Cylindrical part
41: Projection pin
42: Hook
D: Draft chamber
Da: Duct hole
Db: Front opening part
Dc: Door
L: Chlorosilane sample solution
r1, r2: Residue
S: Sample for analyzing

The invention claimed is:

1. An analysis apparatus of chlorosilanes, which is in communication with an atmosphere external to the analysis apparatus, comprising:
   a draft chamber having a top, a bottom, and walls which communicates with the atmosphere external to the analysis apparatus;
   a vaporizer contained in the draft chamber for vaporizing chlorosilanes; and
   an analyzer for analyzing evaporation residues;
wherein the vaporizer comprises:
   a hotplate,
   a cover detachably attached onto the hotplate composing a heating chamber, in contact with an atmosphere external to the analysis apparatus, together with the hotplate, and
   one or more of sample vessels, in which their upside are open to store the chlorosilanes in them, arranged in the heating chamber; and
wherein the cover comprises:
   a supply port for supplying an inert gas or nitrogen gas into the heating chamber and
   a discharge port for discharging gases in the heating chamber.

2. The analysis apparatus of claim 1, wherein the cover comprises a single supply port and a plurality of discharge ports.

3. The analysis apparatus of claim 1, wherein the supply port can have a nozzle with a plurality of supply ports.

4. The analysis apparatus of claim 1, wherein the discharge ports communicate with a box on and abutting the cover of the heating chamber.

5. The analysis apparatus of claim 1, wherein the discharge ports communicate with a box connected to and abutting the cover of the heating chamber.

6. The analysis apparatus of claim 1, wherein a height of a lower edge of the supply port is equal to a height of a lower edge of the discharge port.

7. The analysis apparatus of chlorosilanes according to claim 1, wherein a heating face of the hotplate, an inner face of the cover, and the sample vessel are made of a fluoride type resin.

8. The analysis apparatus of chlorosilanes according to claim 7, wherein the supply port and the discharge port are located at higher places than positions of upper ends of the sample vessels.

9. The analysis apparatus of chlorosilanes according to claim 1, wherein the supply port and the discharge port are located at higher places than positions of upper ends of the sample vessels.

10. The analysis apparatus of claim 9, wherein the supply port and the discharge port are arranged on side walls facing each other.

11. An analysis method of chlorosilanes, using an analysis apparatus in communication with an atmosphere external to the analysis apparatus, comprising:

a vaporization process for vaporizing chlorosilanes and
an analysis process for analyzing an evaporation residue
wherein the vaporization process comprises steps in which
   the chlorosilanes are stored in sample vessels,
   the sample vessels are arranged in a heating chamber in contact with an atmosphere external to the analysis apparatus, and
   the heating chamber is heated with an inert gas flowing through the heating chamber.

12. The analysis method of chlorosilanes according to claim 11, wherein a plurality of reference vessels, in which the chlorosilanes are not stored, are arranged in the heating chamber together with the sample vessels during the vaporization process.

13. The analysis method of claim 11, wherein the inert gas supplied in the heating chamber through a supply port flows toward a discharge port together with a vapor of vaporized chlorosilanes derived from the sample vessels.

14. The analysis method of claim 11, wherein nitrogen gas is charged to the heating chamber.

* * * * *